United States Patent
Lord

(10) Patent No.: US 9,497,999 B2
(45) Date of Patent: *Nov. 22, 2016

(54) ELECTRONIC VAPOR PROVISION DEVICE

(71) Applicant: NICOVENTURES HOLDINGS LIMITED, London (GB)

(72) Inventor: Christopher Lord, London (GB)

(73) Assignee: NICOVENTURES HOLDINGS LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/401,501

(22) PCT Filed: May 14, 2013

(86) PCT No.: PCT/EP2013/059946
§ 371 (c)(1),
(2) Date: Nov. 14, 2014

(87) PCT Pub. No.: WO2013/171215
PCT Pub. Date: Nov. 21, 2013

(65) Prior Publication Data
US 2015/0128965 A1    May 14, 2015

(30) Foreign Application Priority Data
May 14, 2012  (GB) .................................. 1208349.9

(51) Int. Cl.
*A24F 47/00* (2006.01)
*H02J 7/34* (2006.01)
(Continued)

(52) U.S. Cl.
CPC .............. *A24F 47/008* (2013.01); *A61M 1/34* (2013.01); *H02J 7/345* (2013.01); *H05B 1/0244* (2013.01)

(58) Field of Classification Search
USPC ................ 392/386–406; 128/200.11–207.18; 320/166–167, 157–159, 162–164
See application file for complete search history.

(56) References Cited

U.S. PATENT DOCUMENTS 4,947,875 A    8/1990 Brooks et al.
5,095,921 A *  3/1992 Losee et al. .................. 131/194
(Continued)

FOREIGN PATENT DOCUMENTS

CA    2641869 A1    5/2010
CN    1284493       11/2006
(Continued)

OTHER PUBLICATIONS

International Search Report and Written Opinion, mailed Sep. 18, 2013, for PCT/EP2013/059946, filed May 14, 2013.
(Continued)

*Primary Examiner* — Michael H Wilson
*Assistant Examiner* — Eric Yaary
(74) *Attorney, Agent, or Firm* — Patterson Thuente Pedersen, P.A.

(57) ABSTRACT

An electronic vapor provision device comprising a battery assembly 8 and a vaporizer 24, wherein the battery assembly 8 comprises a power cell 10 and a computer 12, the vaporizer 24 is releasably connectable to the battery assembly 8 and the computer 12 comprises a computer processor 16 and a memory 18; wherein the computer 12 is configured to detect whether the vaporizer 24 is connected to the battery assembly 8; the battery assembly 8 further comprises a capacitor 38; and the computer 12 is configured to first charge the capacitor 38 and then detect whether a vaporizer 24 is connected to the battery assembly 8 by measuring whether the capacitor 38 is discharged.

15 Claims, 4 Drawing Sheets

(51) Int. Cl.
*A61M 1/34* (2006.01)
*H05B 1/02* (2006.01)

(56) References Cited

U.S. PATENT DOCUMENTS

| | | | |
|---|---|---|---|
| 5,144,962 A | 9/1992 | Counts et al. | |
| 5,372,148 A * | 12/1994 | McCafferty et al. | 131/194 |
| 5,661,470 A * | 8/1997 | Karr | 340/10.33 |
| 2003/0179003 A1* | 9/2003 | Toda et al. | 324/679 |
| 2005/0016550 A1 | 1/2005 | Katase | |
| 2005/0058441 A1* | 3/2005 | Kameyama et al. | 396/6 |
| 2005/0166076 A1 | 7/2005 | Truong | |
| 2005/0268911 A1 | 12/2005 | Cross et al. | |
| 2007/0267031 A1 | 11/2007 | Hon | |
| 2009/0058578 A1 | 3/2009 | Huang | |
| 2009/0095311 A1 | 4/2009 | Han | |
| 2009/0230117 A1 | 9/2009 | Fernando et al. | |
| 2010/0052660 A1 | 3/2010 | Wang | |
| 2011/0210746 A1* | 9/2011 | Yugou et al. | 324/427 |
| 2011/0226266 A1 | 9/2011 | Tao | |
| 2011/0265806 A1 | 11/2011 | Alarcon et al. | |
| 2012/0227753 A1 | 9/2012 | Newton | |
| 2012/0318882 A1 | 12/2012 | Abehasera | |
| 2013/0037041 A1 | 2/2013 | Worm et al. | |
| 2013/0042865 A1 | 2/2013 | Monsess et al. | |
| 2013/0169230 A1 | 7/2013 | Li et al. | |
| 2013/0207455 A1* | 8/2013 | Doljack | 307/9.1 |
| 2015/0047661 A1* | 2/2015 | Blackley et al. | 131/329 |
| 2015/0114408 A1 | 4/2015 | Lord | |
| 2015/0128965 A1 | 5/2015 | Lord | |
| 2015/0128966 A1 | 5/2015 | Lord | |
| 2015/0136153 A1 | 5/2015 | Lord | |
| 2015/0257448 A1 | 9/2015 | Lord | |

FOREIGN PATENT DOCUMENTS

| | | |
|---|---|---|
| CN | 201393548 Y | 2/2010 |
| CN | 101969800 | 2/2011 |
| CN | 101977522 | 2/2011 |
| CN | 201821914 U | 5/2011 |
| CN | 102264251 | 11/2011 |
| CN | 202474905 U | 10/2012 |
| CN | 203504217 U | 3/2014 |
| DE | 202005018998 U1 | 2/2006 |
| EP | 2100525 A1 | 9/2009 |
| EP | 2201850 A1 | 6/2010 |
| EP | 2 383 861 A2 | 11/2011 |
| EP | 2404515 A1 | 1/2012 |
| GB | 2468932 A | 9/2010 |
| JP | 201290427 | 5/2012 |
| WO | WO 2007074430 A1 | 7/2007 |
| WO | WO 2009032064 A2 | 3/2009 |
| WO | 2009118085 A1 | 10/2009 |
| WO | 2010091593 | 8/2010 |
| WO | 2010118644 A1 | 10/2010 |
| WO | WO 2011137453 A2 | 11/2011 |
| WO | 2011147699 A1 | 12/2011 |
| WO | WO 2013025921 A1 | 2/2013 |

OTHER PUBLICATIONS

Vaishali et al., Random and Periodic Sleep Schedules for Target Detection in Sensor Networks, Journal of Computer Science and Technology, May 2008, 23(3) pp. 343-354.

Load Detecting Power Supply (National Semiconductor RD-166 Production Applications Design Center) Dec. 2008.

Application and File History for U.S. Appl. No. 14/401,508, filed Nov. 14, 2014, inventor Lord.

PCT International Search Report and Written Opinion of the International Searching Authority for PCT/GB2014/052625, mailed Feb. 6, 2015, 17 pages.

PCT International Preliminary Report on Patentability for PCT/GB2014/052625, mailed Dec. 3, 2015, 22 pages.

Chinese First Office Action from Chinese Application No. 201380025459.0 dated Feb. 14, 2016. English translation is provided.

International Preliminary Report on Patentability mailed Apr. 23, 2014 for PCT/EP2013/059936 filed May 14, 2013.

Application and File History for U.S. Appl. No. 14/912,598, filed Feb. 17, 2016, inventors Lord et al.

Application and Filing Receipt for U.S. Appl. No. 15/027,344, filed Apr. 4, 2016, inventors Lord et al.

Chinese Office Action, Chinese Patent Application No. 201380025843.7, mailed May 4, 2016, 9 pages.

* cited by examiner

ELECTRONIC VAPOR PROVISION DEVICE

CLAIM FOR PRIORITY

This application is the National Stage of International Application No. PCT/EP2013/059946, filed May 14, 2013, which in turn claims priority to and benefit of British Patent Application No. GB1208349.9, filed May 14, 2012. The entire contents of the aforementioned applications are herein expressly incorporated by reference.

FIELD

The specification relates to electronic vapour provision devices. More particularly, but not exclusively, the specification concerns electronic vapour provision devices such as electronic cigarettes.

BACKGROUND

Electronic vapour provision devices are typically cigarette-sized and function by allowing a user to inhale a nicotine vapour from a liquid store by applying a suction force to a mouthpiece. Some electronic vapour provision devices have an airflow sensor that activates when a user applies the suction force and causes a heater coil to heat up and vaporise the liquid. Electronic vapour provision devices include electronic cigarettes.

SUMMARY

In an embodiment there is provided an electronic vapour provision device comprising a battery assembly and a vaporiser, where the battery assembly comprises a power cell and a computer, the vaporiser is releasably connectable to the battery assembly and the computer comprises a computer processor and a memory; wherein the computer is configured to detect whether the vaporiser is connected to the battery assembly; the battery assembly further comprises a capacitor; and the computer is configured to first charge the capacitor and then detect whether a vaporiser is connected to the battery assembly by measuring whether the capacitor is discharged.

This has the advantage that the technical interaction between the computer and the vapour provision device enables the computer to distinguish between a vaporiser connected state and a vaporiser non connected state. The device can then be configured accordingly.

The computer may be configured to substantially remain in a sleep mode until the vaporiser is connected to the battery assembly. Moreover, the sleep mode may be a low power mode.

By remaining in a low power sleep mode the device remains active yet consumes very little power. This has the advantage that the device can be charged, for instance during manufacture, and remain in a sleep mode until purchased and used by a consumer. The device will therefore have sufficient power remaining to be used without first charging the device. This also provides an efficient use of power and minimises energy wastage. The device has a further advantage that it can remain in a low power mode without the additional use of a switch to deactivate and activate.

The computer can be configured to enter a connected mode when the vaporiser is connected to the battery assembly. Furthermore, the electronic vapour provision device may use less power in sleep mode than in connected mode.

Advantageously, once the vaporiser has been connected, the connected mode is a higher power state to enable a more rapid activation once the device is activated by a user.

The computer may be configured to wake from sleep mode after a predetermined sleep time to determine whether the vaporiser is connected to the battery assembly. Moreover, the computer may be configured to re-enter sleep mode if a vaporiser is not connected to the battery assembly.

The computer can be configured such that the time between entering consecutive sleep modes when the vaporiser is not connected is less that the sleep time.

The device may enter a low power sleep mode, then wake to test connection before quickly re-entering a low power sleep mode. This maintains a low power usage while in a sleep mode and between sleep modes. The sleep time may have a value between 0.5 and 5 seconds.

The computer may be configured to enter a sleep mode when the capacitor is not substantially fully discharged. Moreover, the computer may be configured to enter a connected mode when the capacitor is substantially fully discharged. In other words, the computer may be configured to determine that the vaporiser is not connected to the battery assembly when the capacitor is not substantially fully discharged.

Furthermore, the computer may be configured to determine that the vaporiser is connected to the battery assembly when the capacitor is substantially fully discharged.

The battery assembly can further comprise first and second battery assembly connection terminals, and the vaporiser can comprise first and second vaporiser connection terminals, such that the vaporiser is connected to the battery assembly when the first battery assembly connection terminal is connected to the first vaporiser connection terminal and the second battery assembly connection terminal is connected to the second vaporiser connection terminal; wherein the capacitor is connected in parallel with the first and second battery assembly connection terminals.

The battery assembly may further comprise a resistor in series with the capacitor; wherein the capacitor and resistor are in parallel with the first and second battery assembly connection terminals.

The computer may be configured to send out a pulse and the capacitor may be charged for a period of time equal to the width of the pulse.

The electronic vapour provision device may further comprise a transistor; wherein the pulse is sent to the transistor and the transistor opens the current from the power cell to the capacitor for a period of time equal to the width of the pulse.

In another embodiment there is provided a method of detecting connection of battery assembly and a vaporiser of an electronic vapour provision device, wherein the battery assembly comprises a power cell, a processor and capacitor; and the vaporiser is releasably connectable to the battery assembly; the method comprising initially charging the capacitor, then measuring whether the capacitor is discharged.

In another embodiment there is provided an electronic vapour provision device comprising a battery assembly and a vaporiser, wherein the battery assembly comprises a power cell and a computer; the vaporiser is releasably-attachable to the battery assembly; the computer comprises a computer processor, a memory and an input-output means; and the computer is configured in use to detect whether the vaporiser is connected to the battery assembly.

As used herein, the term vapour includes an aerosol and other fluid streams for provision to a user by the electronic vapour provision device.

BRIEF DESCRIPTION OF THE DRAWINGS

For a better understanding of the disclosure, and to show how example embodiments may be carried into effect, reference will now be made to the accompanying drawings in which.

DETAILED DESCRIPTION

Figure 1:
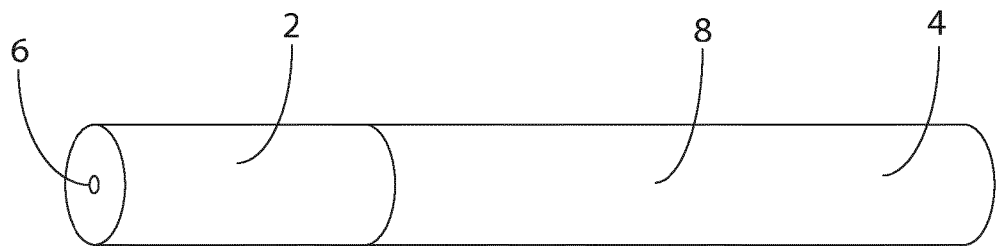
FIG. 1 is a side perspective view of an electronic vapour provision device.
Figure 2:
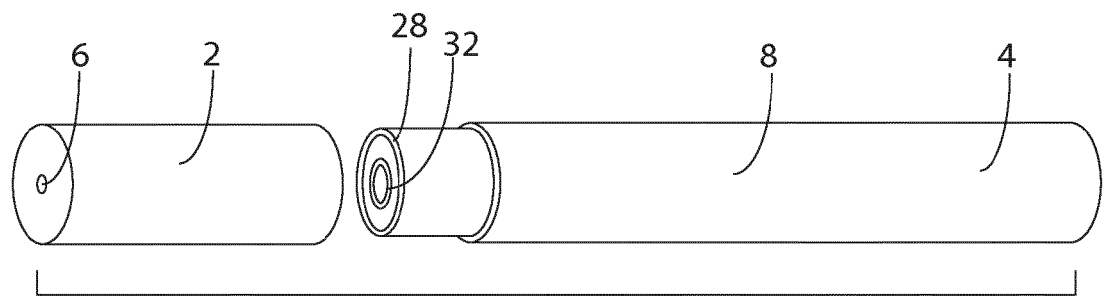
FIG. 2 is an exploded side perspective view of the electronic vapour provision device of FIG. 1.
Figure 3:
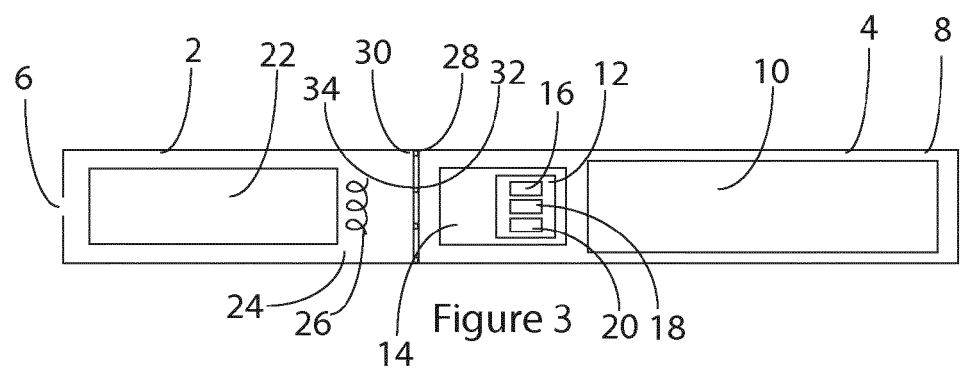
FIG. 3 is a side sectional view through the device of FIG. 1.

Referring to FIGS. 1 to 3 there is shown an electronic vapour provision device, also referred to herein as an electronic smoking device, that comprises a mouthpiece 2 and a body 4. The electronic vapour provision device is shaped like a conventional cigarette. Both the mouthpiece 2 and body 4 are cylindrical and are configured to connect to each other coaxially so as to form the conventional cigarette shape. The mouthpiece 2 is connectable to the body 4 at a first end of the mouthpiece and has an air outlet 6 at a second end. The body 2 comprises a battery assembly 8, comprising a power cell 10 and a computer 12 on a circuit board 14, wherein the power cell 10 is connected to the computer 12. The computer 12 comprises a computer processor 16, a memory 18 and input-output arrangement 20. In this example the computer 12 is a microcontroller. The computer 12 is configured to control and interface with the other electrical components of the battery assembly 8, comprising the power cell 10, via the input-output arrangement 20.

The mouthpiece 2 comprises a liquid bottle 22 and a vaporiser 24 having a heater coil 26. For example, the vaporiser 24 is in fluid communication with the liquid bottle 22. The mouthpiece 2 is connectable to the battery assembly 8 by a screw thread, wherein connection of the battery assembly 8 and the mouthpiece 2 connects a first battery assembly terminal 28 to a first vaporiser terminal 30 and a second battery assembly terminal 32 to a second vaporiser terminal 34, forming an electrically conductive contact in both cases. The vaporiser terminals 30 34 are electrically connected in parallel to the vaporiser 24.

The herein described configuration of the computer 12 comprises the computer operating according to a computer program stored in its memory 18 and accessed by its computer processor 16.

To maximise the lifetime of the charge in the power cell 10, the computer 12 is configured to detect whether the vaporiser 24 is connected to the battery assembly 8, the connection state, and to enter a low power sleep mode if the vaporiser 24 is not connected. For example, sleep mode may comprise the computer 12 consuming minimal power and performing no processing. A period during which the computer 12 is in sleep mode is herein referred to as sleep time. Furthermore, if the computer 12 determines that the vaporiser 24 is connected, the computer 12 is configured to enter a connected mode, which is of a higher power than the low power mode.

Moreover, detecting the connection state may comprise the computer 12 periodically checking whether the vaporiser 24 is connected to the battery assembly 8. If the computer 12 determines that the vaporiser 24 is not attached, the computer 12 goes into sleep mode for two seconds. After the sleep time, the computer 12 wakes and immediately and quickly checks again for a vaporiser connection. Again, if the vaporiser is not connected the computer 12 goes into sleep mode for another two seconds. The time that the computer 12 is awake is extremely short compared to the sleep time so the circuit remains predominantly in a low power mode, thus conserving power. During the sleep time no checks are made to determine whether the vaporiser 24 is connected. A user may take several seconds to assemble the device, connecting the vaporiser 24 and the battery assembly 8, so the vaporiser 24 connection may be easily established by the computer 12 before use of the device by a user.

The waking of the computer 12 may for example comprise the computer 12 entering a waking mode distinct from the sleep mode and the connection mode.

The computer 12 checking whether the vaporiser 24 is connected to the battery assembly 8 may for example comprise the computer 12 sending an electrical pulse to the battery assembly terminals 28, 32. For example, the computer 12 may control the power cell 10 so as to supply a pulse of current to the first battery assembly terminal 28 and may measure the current reaching the second the battery assembly terminal 32, for example using a digital multimeter of the battery assembly 8. The digital multimeter is reference 44 in the circuit diagram of FIG. 10. Furthermore, if the vaporiser 24 is connected, the digital multimeter reads a current reaching the second battery assembly terminal 32 via the vaporiser 24 and provides information to the computer 12 indicating this.

Figure 4:
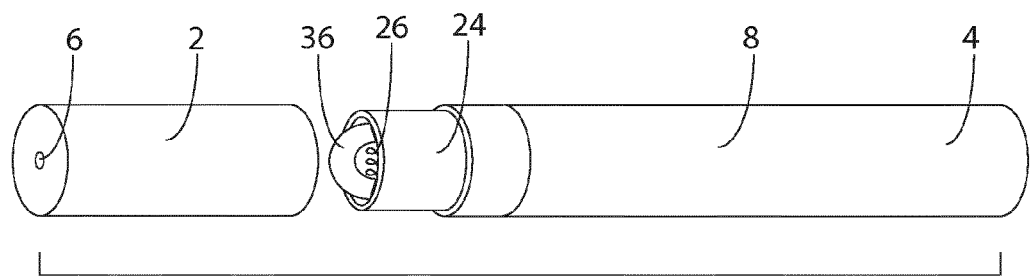
FIG. 4 is a side perspective view of an electronic vapour provision device with separated mouthpiece and body.
Figure 5:
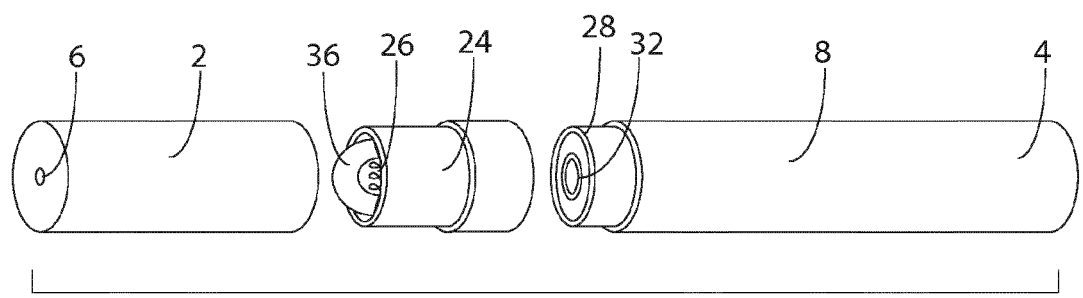
FIG. 5 is a side perspective view of an electronic vapour provision device with separated mouthpiece, vaporiser and battery assembly.
Figure 6:
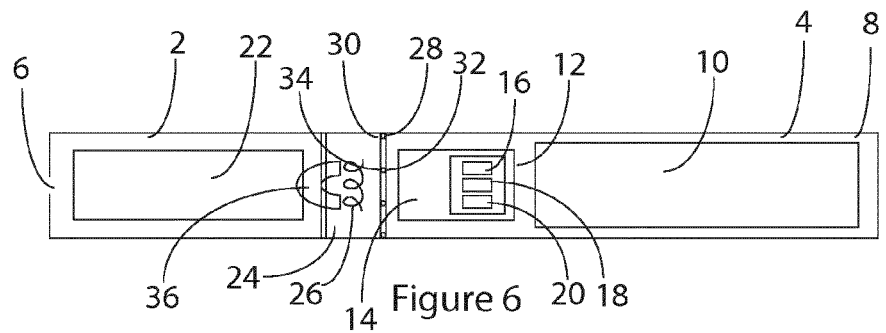
FIG. 6 is a side sectional view through the electronic vapour provision device of FIG. 4 with connected mouthpiece and body.

FIGS. 4 to 6 show another example of an electronic vapour provision device. This device is similar to that shown in FIGS. 1 to 3, however in this example the vaporiser 24 does not form part of the mouthpiece 2. The mouthpiece 2 contains a liquid bottle 22 and is attachable to the vaporiser 24. The vaporiser 24 has a heater coil 26 and additionally a wick 36. For example the wick 36 may be a mesh wick. The mouthpiece 2 and the vaporiser 24 are configured to connect to each other such that the wick 36 acts to communicate liquid from the liquid container 22 onto the vaporiser 24. The interaction between the vaporiser 24 and the battery assembly 8 to conserve power is as described above.

Further examples of how, in the devices of FIGS. 1 to 6, connection of the vaporiser 24 to the body 4 may be detected by the computer 12 are now described with reference to FIGS. 7 to 10.

Figure 7:
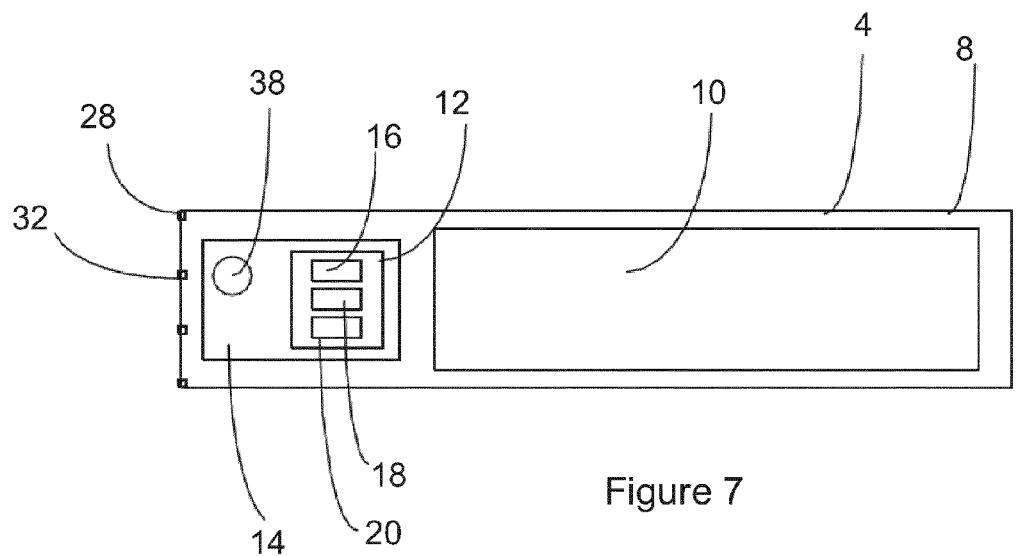
FIG. 7 is a side sectional view of a battery assembly having a capacitor.
Figure 8:
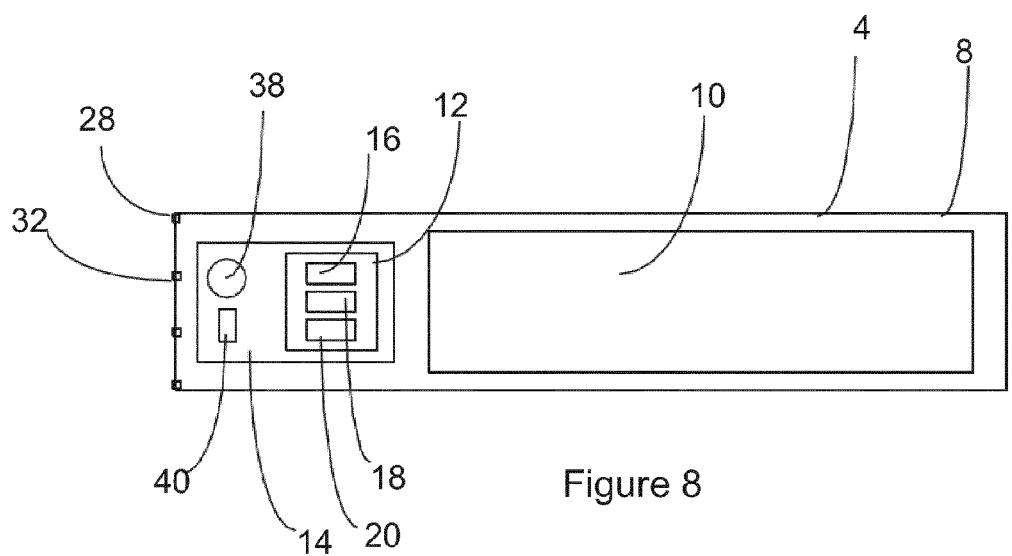
FIG. 8 is a side sectional view of a battery assembly having a capacitor and resistor.

FIG. 7 shows a battery assembly 8 similar to that shown in FIG. 3 and FIG. 6, additionally comprising a capacitor 38. The capacitor 38 is arranged in a circuit such that it is in parallel to the battery assembly terminals and to the power cell 10. To test whether the vaporiser 24 is connected to the battery assembly 8, the computer 12 first controls the power cell 10 to charge the capacitor 38, then waits a short time and checks the charge of the capacitor 38. For example, the computer 12 may use a digital mulitmeter of the battery assembly 8, wired in a switched parallel circuit to the capacitor 38, to check the charge of the capacitor 38. For instance, in order to check the charge of the capacitor 38, the computer 12 may trigger the completion of the switched digital mulitmeter circuit and may then receive information from the mulitmeter indicating a voltage across the capacitor 38 resulting from the charge of the capacitor. If the vaporiser 24 is connected, the resistance of the vaporiser 24 causes the capacitor 38 to discharge quickly so the computer 12 measures at least a substantially fully discharged capacitor 38. If the vaporiser 24 is not connected the capacitor is not substantially fully discharged when checked by the computer 12. FIG. 8 shows an arrangement similar to that shown in FIG. 7, additionally comprising a resistor 40 in series with the capacitor 38. For example, the resistor 40 and the capacitor 38 may be connected in series with each other and in parallel with the first and second battery assembly connection terminals 28 32.

The battery assembly 8 of the devices described herein may further comprise an air pressure sensor, wherein the air pressure sensor is powered by the power cell 10 and controlled by the computer 12. Once the vaporiser is connected to the battery assembly 8, and the device enters a connected mode after the computer 12 has determined the device's connection state, in order to use the device the user must suck on the mouthpiece 2. The electronic vapour provision device is configured such that the user sucking on the mouthpiece 2 causes a drop in air pressure at the air pressure sensor. The computer 12 therefore receives information from the air pressure sensor indicating that a user is sucking on the device. In response to this information, the computer 12 controls the power cell 10 to power the vaporiser 24. For example, the computer may control the power cell 10 to power the vaporiser 24 via the respective first and second terminals of both the battery assembly and the vaporiser. This causes the vaporisation of liquid communicated to the vaporiser 24 from the liquid bottle 22. The provided vapour then passes to the user. Consequently, use of the device by a user comprises the user sucking on the device and the detection of this user interaction by the device so as to trigger the vaporisation of the liquid contained in the device. The pressure sensor is referenced 43 in the circuit of FIG. 10 described in more detail hereinafter.

It should be noted that the herein described configuration of the computer 12 to determine whether the vaporiser 24 is connected to the battery assembly 8 does not require use of the device by the user.

Figure 9:
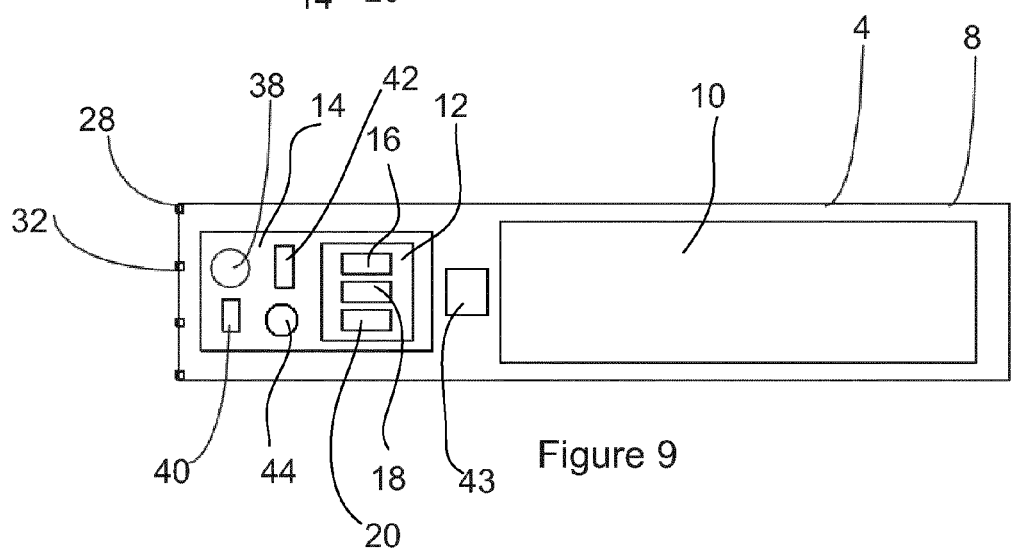
FIG. 9 is a side sectional view of a battery assembly having a capacitor, resistor and transistor.
Figure 10:
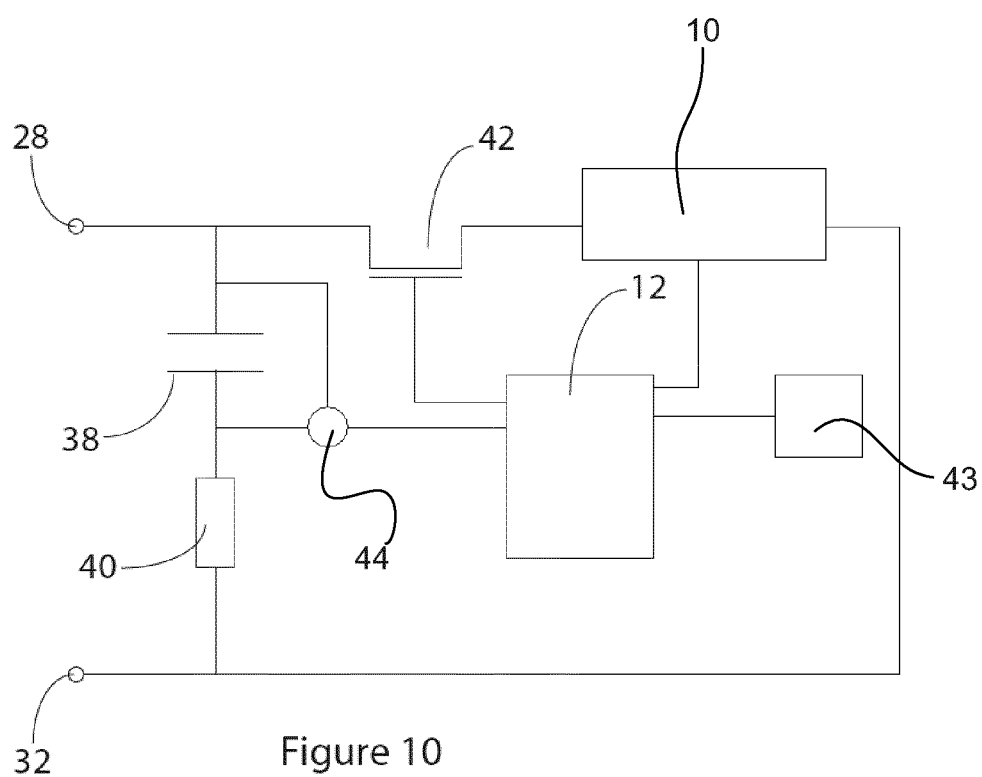
FIG. 10 is a circuit diagram for the battery assembly of FIG. 9.

FIG. 9 shows a battery assembly 8, comprising a digital multimeter 44, similar to that described with reference to FIGS. 7 and 8, further comprising a transistor 42 and the previously described air pressure sensor 43. FIG. 10 shows a circuit diagram of the battery assembly of FIG. 9.

The transistor 42 is connected in series between the power cell 10 and the capacitor 38.

In the example shown in FIG. 9 and FIG. 10, the previously described controlling of the charging of the capacitor 38 by the computer 12 involves the transistor 42. To test whether the vaporiser 24 is connected, the computer 12 sends a square wave pulse to the transistor 42. The transistor 42 supplies current to the capacitor 38 for a period of time equal to the width of the pulse, thereby charging the capacitor 38. For example the transistor 42 may be configured such that it opens a current from the power cell 10 to the capacitor 38 for a period of time equal to the width of the pulse. As described above, if the vaporiser 24 is connected the computer 12 measures at least a substantially fully discharged capacitor 38.

With regard to the embodiments described herein, the following alternatives and variations will now be described.

The electronic vapour provision devices described may be electronic cigarettes.

The sleep time may be substantially 2 seconds. However, the sleep time is not restricted to 2 seconds and other suitable values could be used. Moreover, the time between entering sleep modes can be significantly less than the sleep time.

The computer processor 16 can be a microprocessor. Moreover, the computer 12 may comprise a microcontroller. Furthermore, a computer such as a microcontroller could utilise a watchdog timer to implement the sleep time wait in the low power mode. Using a microcontroller has space saving advantages since the entire computer is located on a single chip and therefore the size of the device is minimised. Fewer components to assemble also provides reduced manufacturing times are costs. The computer is not restricted to being a microcontroller and could be fabricated from separate processor, memory and input-output components.

The device is not restricted to being cigarette shaped.

The vaporiser 24 and the battery assembly 8 may be releasably connectable to each other.

The vaporisers 24 described are examples only.

Moreover, the sleep mode may be the lowest non-zero power mode of the device. Although an air pressure sensor 43 is described, other configurations may be employed to detect when a user is attempting to use the device. For example, an airflow sensor may be used and the device may be configured such that sucking on the mouthpiece 2 by a user causes a flow of air past the air flow sensor.

Although a liquid bottle 22 is described, other types of liquid storage may be used. For example the device may comprise foam partially saturated in liquid for vaporisation.

Although a digital multimeter 44 is described as being used by the computer 12 to determine the level of charge of the capacitor, other suitable configurations may be employed for this purpose. For example, a digital voltmeter may instead be used.

The pulse provided by the computer may be a square wave pulse.

Although examples have been shown and described it will be appreciated by those skilled in the art that various changes and modifications might be made without departing from the scope of the invention.

In order to address various issues and advance the art, the entirety of this disclosure shows by way of illustration various embodiments in which the claimed invention(s) may be practiced and provide for superior electronic vapour provision devices. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilised and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future. Any feature of any embodiment can be used independently of, or in combination with, any other feature.

The invention claimed is:

1. An electronic vapor provision device comprising:
a battery assembly including a power cell, a capacitor, and a computer, the computer having a computer processor and a memory; and
a vaporizer, releasably connectable to the battery assembly,
the computer configured to:
first charge the capacitor; and
then detect whether the vaporizer is connected to the battery assembly by measuring whether the capacitor is discharged.

2. The electronic vapor provision device of claim 1, wherein the computer is further configured to substantially remain in a sleep mode until the vaporizer is connected to the battery assembly.

3. The electronic vapor provision device of claim 2, wherein the sleep mode is a low-power mode.

4. The electronic vapor provision device of claim 2, wherein the computer is further configured to enter a connected mode when the vaporizer is connected to the battery assembly.

5. The electronic vapor provision device of claim 4, wherein the electronic vapor provision device is configured to use less power in the sleep mode than in the connected mode.

6. The electronic vapor provision device of claim 2, wherein the computer is further configured to wake from the sleep mode after a predetermined sleep time to determine whether the vaporizer is connected to the battery assembly.

7. The electronic vapor provision device of claim 6, wherein the computer is configured to re-enter the sleep mode if a vaporizer is not connected to the battery assembly.

8. The electronic vapor provision device of claim 6, wherein the computer is configured such that a time between consecutive sleep modes when the vaporizer is not connected is less than the predetermined sleep time.

9. The electronic vapor provision device of claim 6, wherein the predetermined sleep time has a value between 0.5 seconds and 5 seconds.

10. The electronic vapor provision device of claim 1, wherein the computer is further configured to determine that the vaporizer is not connected to the battery assembly when the capacitor is not substantially fully discharged, and/or to determine that the vaporizer is connected to the battery assembly when the capacitor is substantially fully discharged.

11. The electronic vapor provision device of claim 10, wherein the battery assembly further includes first and second battery assembly connection terminals, and the vaporizer comprises first and second vaporizer connection terminals, such that the vaporizer is connected to the battery assembly when the first battery assembly connection terminal is connected to the first vaporizer connection terminal and the second battery assembly connection terminal is connected to the second vaporizer connection terminal; and wherein the capacitor is connected in parallel with the first and second battery assembly connection terminals.

12. The electronic vapor provision device of claim 11, wherein the battery assembly further includes a resistor in series with the capacitor, and the capacitor and resistor are in parallel with the first and second battery assembly connection terminals.

13. The electronic vapor provision device of claim 1, wherein the computer is further configured to send out a pulse such that the capacitor is charged for a period of time substantially equal to the width of the pulse.

14. The electronic vapor provision device of claim 13, further comprising: a transistor, the electronic vapor provision device configured such that the pulse is sent to the transistor, thereby allowing current to flow from the power cell to the capacitor.

15. A method of detecting connection of a battery assembly and a vaporizer of an electronic vapor provision device, the method comprising:
initially charging a capacitor of a battery assembly, the battery assembly having a power cell, a processor and the capacitor, and
then measuring whether the capacitor is discharged to detect whether the battery assembly is connected to a releasably connectable vaporizer.

* * * * *